United States Patent
Igarashi

(10) Patent No.: US 10,632,244 B2
(45) Date of Patent: Apr. 28, 2020

(54) PLATELET COLLECTION METHOD AND PLATELET COLLECTION SYSTEM

(71) Applicant: TERUMO KABUSHIKI KAISHA, Tokyo (JP)

(72) Inventor: Masatsugu Igarashi, Shizuoka (JP)

(73) Assignee: Terumo Kabushiki Kaisha, Tokyo (JP)

(*) Notice: Subject to any disclaimer, the term of this patent is extended or adjusted under 35 U.S.C. 154(b) by 192 days.

(21) Appl. No.: 15/756,201

(22) PCT Filed: Aug. 25, 2016

(86) PCT No.: PCT/JP2016/074819
§ 371 (c)(1),
(2) Date: Jul. 31, 2018

(87) PCT Pub. No.: WO2017/038624
PCT Pub. Date: Mar. 9, 2017

(65) Prior Publication Data
US 2019/0083696 A1 Mar. 21, 2019

(30) Foreign Application Priority Data
Aug. 28, 2015 (JP) ................ 2015-169618

(51) Int. Cl.
*A61M 1/36* (2006.01)
*A61M 1/02* (2006.01)
(Continued)

(52) U.S. Cl.
CPC ........ *A61M 1/3693* (2013.01); *A61M 1/0272* (2013.01); *A61M 1/0281* (2013.01);
(Continued)

(58) Field of Classification Search
CPC .. A61M 1/0272; A61M 1/0281; A61M 1/029; A61M 2202/0415;
(Continued)

(56) References Cited

U.S. PATENT DOCUMENTS

| | | |
|---|---|---|
| 6,200,287 B1 | 3/2001 | Keller et al. |
| 8,523,750 B2 | 9/2013 | Pittinger et al. |
| 2008/0035585 A1* | 2/2008 | Antwiler ............. A61M 1/3693 210/787 |

FOREIGN PATENT DOCUMENTS

| | | |
|---|---|---|
| EP | 2839741 A1 | 2/2015 |
| WO | 2011084348 A2 | 7/2011 |

(Continued)

OTHER PUBLICATIONS

European Searching Authority; European Search Report; dated Mar. 14, 2019, 6 pages.

*Primary Examiner* — Timothy C Cleveland
(74) *Attorney, Agent, or Firm* — Terumo BCT, Inc IP Law Dept

(57) ABSTRACT

A platelet collection method includes a step of accommodating whole blood in a first chamber (44) and performing centrifugal separation, a step of transferring a buffy coat resulting from the centrifugal separation to a second chamber (50), and a step of performing centrifugal separation on the buffy coat. Subsequently, a step of transferring a platelet-containing component resulting from the centrifugal separation to a third chamber (52) and a step of performing centrifugal separation on the platelet-containing component are executed. Also performed in the collection method are a step of introducing a platelet additive solution into the third chamber (52) and replacing plasma resulting from the centrifugal separation and a step of collecting platelets remaining in the third chamber (52) along with the platelet additive solution.

13 Claims, 11 Drawing Sheets

(51) Int. Cl.
    *A61M 1/38*          (2006.01)
    *B04B 5/04*          (2006.01)
    *B04B 5/10*          (2006.01)

(52) U.S. Cl.
    CPC .............. *A61M 1/38* (2013.01); *B04B 5/0442* (2013.01); *B04B 5/10* (2013.01); *A61M 2202/0415* (2013.01); *A61M 2202/0427* (2013.01); *B04B 2005/0471* (2013.01)

(58) Field of Classification Search
    CPC ......... A61M 2202/0427; B04B 5/0442; B04B 2005/0471
    See application file for complete search history.

(56) References Cited

FOREIGN PATENT DOCUMENTS

| | | |
|---|---|---|
| WO | 2012-139017 A1 | 10/2012 |
| WO | 2012139017 A1 | 10/2012 |

\* cited by examiner

PLATELET COLLECTION METHOD AND PLATELET COLLECTION SYSTEM

TECHNICAL FIELD

The present invention relates to a collection method and a collection system for separating a biological component from a liquid containing at least one biological component and restoring the biological component and, more particularly, to a platelet collection method and a platelet collection system for collecting platelets from blood by centrifugal separation.

BACKGROUND ART

A patient may develop side effects of blood transfusion during blood transfusion of a platelet preparation. The plasma that is included in the platelet preparation is regarded as a cause of the side effects. Accordingly, platelets with a low plasma content (washed platelets: also referred to as washed platelet concentrates) are desired at blood transfusion sites.

JP 2013-514863 A discloses a blood apheresis system collecting platelets by performing centrifugal separation on whole blood taken from a donor. The system that is disclosed in JP 2013-514863 A is configured to obtain washed platelets by allowing a platelet-containing component and a platelet additive solution to simultaneously flow into a chamber during the centrifugal separation.

SUMMARY OF INVENTION

The present invention has been made in relation to the platelet collection technique described above, and an object thereof is to provide a platelet collection method and a platelet collection system allowing washed platelets with a sufficiently low plasma content to be further reliably and efficiently obtained.

In order to achieve the above object, a platelet collection method according to the present invention includes a step of accommodating whole blood collected from a donor in a first chamber and separating the whole blood into a first blood component including a large number of platelets and a remaining component by performing centrifugal separation, a step of transferring the first blood component from the first chamber to a second chamber, a step of separating the first blood component transferred to the second chamber into a platelet-containing component and a second blood component by performing centrifugal separation, a step of transferring the platelet-containing component from the second chamber to a third chamber, a step of separating the platelet-containing component transferred to the third chamber into platelets and another component by performing centrifugal separation, a step of introducing a platelet additive solution into the third chamber and replacing the other component with the platelet additive solution, and a step of collecting the platelets remaining in the third chamber along with the platelet additive solution.

By the platelet collection method described above, washed platelets can be obtained by the platelet-containing component transferred to the third chamber being separated into the platelets and the other component (plasma) as a result of the centrifugal separation and the other component being replaced with the platelet additive solution. As a result, the washed platelets with a sufficiently low plasma content can be further reliably and efficiently obtained by the other component being easily removed from the platelet-containing component. A reduction in side effects of blood transfusion can be anticipated from the generated washed platelets.

In this case, it is preferable that a centrifugal force differing from the centrifugal force that is applied to the first and second chambers is applied to the third chamber during the centrifugal separation in the third chamber.

By the platelet collection method, the centrifugal force differing from the centrifugal force that is applied to the first and second chambers is applied during the centrifugal separation in the third chamber as described above. Accordingly, the platelet-containing component can be separated into the platelets and the other component in a satisfactory manner.

In addition to the above configuration, the third chamber may have two outlets having different distances from a centrifugal center at the time of the centrifugal separation.

By the third chamber having the two outlets having the different distances as described above, an outflow of the plasma and the platelet additive solution can be easily performed from one of the outlets and an outflow of the washed platelets can be easily performed from the other outlet.

In addition, the blood component of the whole blood may flow in sequence through the first to third chambers communicating with one another via a tube.

As a result, the blood component flows through the first to third chambers in sequence and continuously. Accordingly, the circuit that collects the platelets from the whole blood is configured in a simple and hygienic manner.

Furthermore, it is preferable that the second chamber is capable of separating leukocytes as the second blood component.

By the leukocytes being separated in the second chamber as described above, mixing of the leukocytes with the platelet-containing component supplied to the third chamber can be suppressed and the washed platelets including few leukocytes can be obtained.

It is preferable that the platelets are allowed to remain in the third chamber by the other component being allowed to flow to an outside of the third chamber while the platelet-containing component is introduced into the third chamber during the centrifugal separation of the platelet-containing component.

As described above, the other component is allowed to flow out while the platelet-containing component is introduced during the centrifugal separation of the platelet-containing component. Accordingly, the platelets can be concentrated in the third chamber by the centrifugal separation of the platelet-containing component being continuously performed.

In addition, the other component may be allowed to flow to a reservoir of the remaining component during the centrifugal separation of the platelet-containing component and the other component and the platelet additive solution may be allowed to flow to a disposal container during the introduction of the platelet additive solution into the third chamber.

An inflow of the platelet additive solution to the donor can be prevented and the plasma can be returned in a satisfactory manner by the flow destination of the other component resulting from the centrifugal separation being selectively changed as described above.

The platelet additive solution may be allowed to flow in from a flow path portion separate from a flow path portion allowing the platelet-containing component to flow into the third chamber during the introduction of the platelet additive solution into the third chamber.

By the platelet additive solution and the platelet-containing component being allowed to flow in from the separate flow path portions as described above, the inflow of the platelet additive solution to the third chamber can be smoothly performed and the replacement with the platelet additive solution can be performed more quickly and stably.

Furthermore, it is preferable that only the platelet additive solution is allowed to flow into the third chamber by the inflow of the platelet-containing component being stopped during the introduction of the platelet additive solution into the third chamber.

The other separated component is replaced further smoothly with the platelet additive solution by only the platelet additive solution being allowed to flow in during the introduction of the platelet additive solution as described above.

Moreover, a speed of the introduction of the platelet additive solution into the third chamber may be higher during the collection of the platelets than during the replacement of the other component with the platelet additive solution.

The platelets aggregated in the third chamber can be recovered as the washed platelets while being broken by the platelet additive solution by the introduction speed of the platelet additive solution being increased during the collection of the platelets as described above.

A platelet collection system according to the present invention includes a primary separation unit including a first chamber accommodating whole blood collected from a donor and separating the whole blood into a first blood component including a large number of platelets and a remaining component by performing centrifugal separation, a secondary separation unit including a second chamber accommodating the first blood component transferred from the primary separation unit and separating the first blood component into a platelet-containing component and a second blood component by performing centrifugal separation, a tertiary separation unit including a third chamber accommodating the platelet-containing component transferred from the secondary separation unit and separating the platelet-containing component into platelets and another component by performing centrifugal separation, and a centrifugal force application unit applying a centrifugal force to the primary to tertiary separation units, in which the tertiary separation unit replaces the other component resulting from the centrifugal separation with a platelet additive solution by the platelet additive solution being introduced after an inflow of the platelet-containing component is stopped and allows the platelets remaining after the replacement to flow out along with the platelet additive solution.

According to the above, the platelet collection system replaces the other component with the platelet additive solution by introducing the platelet additive solution after the inflow of the platelet-containing component to the third chamber is stopped, and thus plasma can be easily removed from the platelet-containing component. Accordingly, washed platelets with a sufficiently low plasma content can be further reliably and efficiently obtained.

In this case, the collection system may include a first flow path portion allowing the platelet-containing component to flow into the third chamber, a second flow path portion allowing the platelet additive solution to flow into the third chamber, a first clamp opening and closing the first flow path portion, and a second clamp opening and closing the second flow path portion. The second clamp may be closed when the first clamp is opened and the second clamp may be opened when the first clamp is closed.

The collection system is capable of easily switching between the supply of the platelet-containing component and the supply of the platelet additive solution to the third chamber by switching the opening and closing of the first and second clamps as described above.

The platelet collection method and the platelet collection system according to the present invention allow washed platelets with a sufficiently low plasma content to be further reliably and efficiently obtained.

DESCRIPTION OF EMBODIMENTS

Hereinafter, a preferred embodiment of a platelet collection method, a platelet collection system, a recovery device, and a separator according to the present invention will be described in detail with reference to accompanying drawings.

The collection system according to the present invention is configured as a blood apheresis system that performs centrifugal separation on the blood of a donor (such as a blood donor and a patient) outside his or her body and collects platelets, which are a blood component in the blood. A collection system for component blood sampling that continuously takes whole blood from a donor, performs centrifugal separation, and returns some blood components to the donor will be described below. The collection system can also be applied to a system performing whole blood sampling by being appropriately modified.

Figure 1:
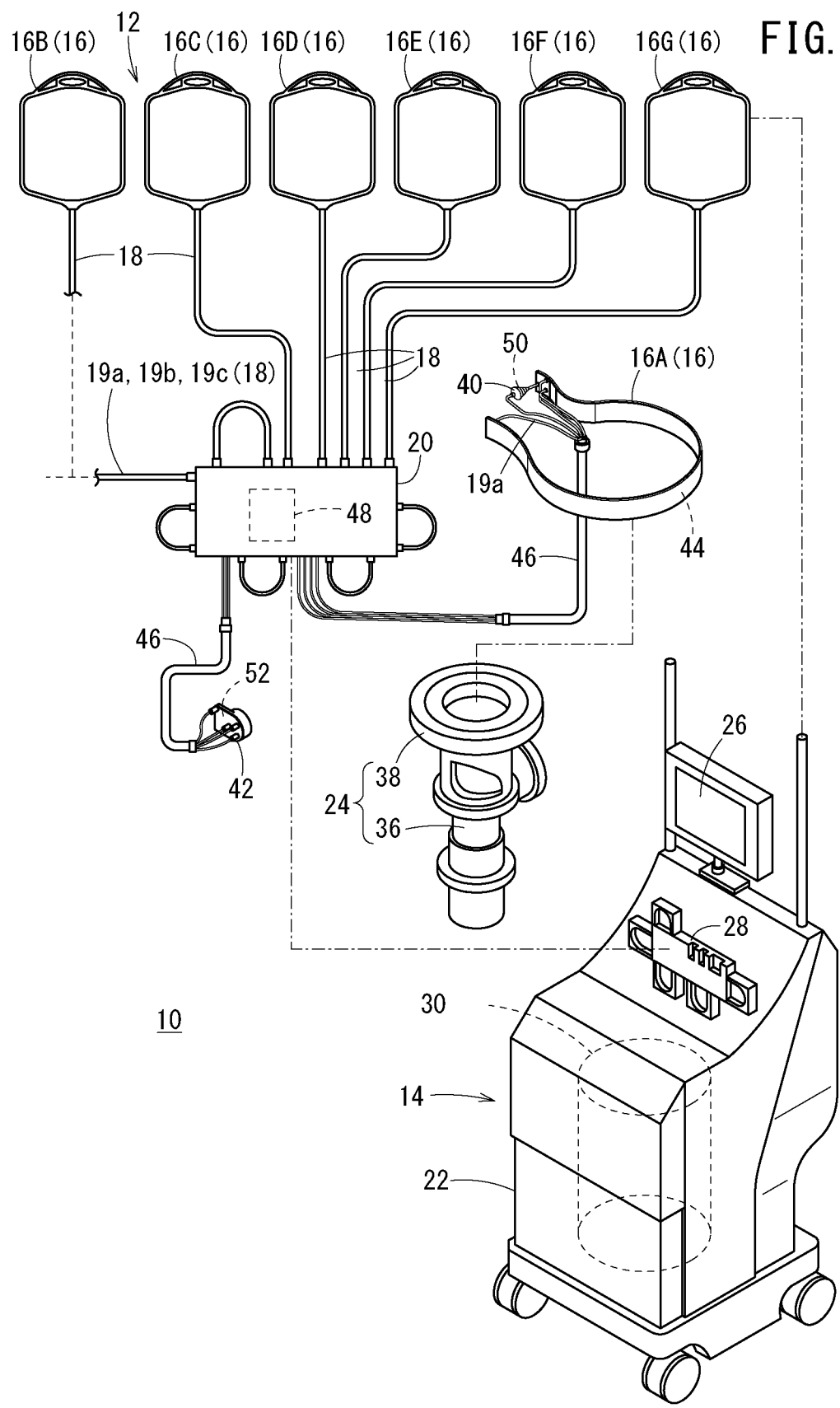
FIG. 1 is an explanatory diagram illustrating an overall configuration of a collection system according to an embodiment of the present invention.

As illustrated in FIG. 1, a collection system 10 includes a blood sampling circuit set 12 (recovery device) for storing a blood component and allowing the blood component to flow and a centrifugal separation device 14 (centrifugal force application unit) applying a centrifugal force to the blood sampling circuit set 12.

For contamination prevention and hygiene, the blood sampling circuit set 12 is disposed of every time the blood sampling circuit set 12 is used. The blood sampling circuit set 12 is provided with a plurality of bags 16, a plurality of tubes 18 leading to the bags 16, and a cassette 20 formed on a predetermined path. The plurality of tubes 18 is held in or connected to the cassette 20. Each of the configurations of the blood sampling circuit set 12 will be described later.

The centrifugal separation device 14 is a piece of equipment repeatedly used for component blood sampling and is provided in a medical facility, a vehicle for blood sampling, or the like. The centrifugal separation device 14 is provided with a box-shaped device main body 22 formed to be relatively long in a height direction and a rotor 24 rotatably accommodated in the device main body 22.

The device main body 22 has a function to accommodate each bag 16 of the blood sampling circuit set 12 inside or hold each bag 16 of the blood sampling circuit set 12 outside and control centrifugal separation of blood taken into the blood sampling circuit set 12. The device main body 22 is provided with a display operation device 26 performing an operation and display at a time when the centrifugal separation of the blood is performed, an attachment portion 28 for attaching the cassette 20 of the blood sampling circuit set 12, and an accommodating space 30 accommodating the rotor 24.

The attachment portion 28 of the device main body 22 is formed in a frame shape on an upper portion side of the device main body 22 and is configured such that the cassette 20 is fitted into and held inside the attachment portion 28. In addition, the attachment portion 28 is provided with a plurality of pumps 32 and a plurality of clamps 34 illustrated in FIG. 2 at predetermined positions and is provided with a plurality of sensors (not illustrated). By the cassette 20 being attached to the attachment portion 28, the pumps 32, the clamps 34, and the sensors are arranged on a path that the tube 18 and the cassette 20 of the blood sampling circuit set 12 constitute.

The accommodating space 30 of the device main body 22 is disposed below the attachment portion 28 and is formed in a cylindrical shape extending along the up-down direction of the device main body 22. A rotary drive source (not illustrated) rotating the rotor 24 attached thereto is disposed in a bottom portion of the accommodating space 30.

The rotor 24 of the centrifugal separation device 14 is configured to be removable from the device main body 22 and allows the blood sampling circuit set 12 to be easily attached. The rotor 24 has a shaft portion 36 elongated in an up-down direction and a conduit housing 38 disposed in an upper end portion of the shaft portion 36. In a state where the rotor 24 is accommodated in the accommodating space 30, a lower end portion of the shaft portion 36 is connected and fixed to the rotary drive source.

The conduit housing 38 is formed in an annular shape and is larger in outer diameter than the shaft portion 36. A primary separation bag 16A, which is a first separation unit of the blood sampling circuit set 12, is mounted along a circumferential direction on the outer peripheral surface of the conduit housing 38. In addition, several cavity portions 38a in which a secondary separator 40 (secondary separation unit) and a tertiary separator 42 (tertiary separation unit, separator) of the blood sampling circuit set 12 are accommodated are disposed in the conduit housing 38 (refer to FIG. 3). The conduit housing 38 integrally rotates with the shaft portion 36 under the control of the device main body 22.

The connection states of each bag 16 and each tube 18 of the blood sampling circuit set 12 will be described below with reference to FIG. 2. The blood sampling circuit set 12 has the primary separation bag 16A, an ACD solution storage bag 16B, an auxiliary bag 16C, an additive solution storage bag 16D, a PPP bag 16E, a disposal bag 16F, and a WPC bag 16G as the plurality of bags 16. An ACD solution, which is a blood anticoagulant, is stored in advance in the ACID solution storage bag 16B, and a platelet additive solution 102 is stored in advance in the additive solution storage bag 16D. The primary separation bag 16A, the auxiliary bag 16C, the PPP bag 16E, the disposal bag 16F, and the WPC bag 16G have cavities capable of accommodating a fluid.

As illustrated in FIG. 1, the primary separation bag 16A is formed as a belt-shaped bag. A first chamber 44 to which the whole blood of a donor is supplied is disposed in the primary separation bag 16A. The primary separation bag 16A is wound around the outer peripheral surface of the conduit housing 38 when the blood sampling circuit set 12 is attached. Alternatively, the conduit housing 38 may also be configured to be provided with a pocket (not illustrated) near the outer periphery thereof to store the primary separation bag 16A. One end portion and the other end portion of the primary separation bag 16A are connected by a connecting body (such as a string, not illustrated) when the conduit housing 38 is mounted.

An introduction tube 19a is connected to one end portion side of the primary separation bag 16A. The introduction tube 19a is held in the cassette 20 through the inside of a bundle tube 46 illustrated in FIG. 1, is exposed to the outside through a predetermined path in the cassette 20, and is connected to a blood inlet-outlet portion (not illustrated) of the donor. The blood inlet-outlet portion is composed of, for example, an indwelling needle that is inserted into and detained in the donor's blood vessel. As illustrated in FIG. 2, a pump 32a suctioning blood from the blood inlet-outlet portion is disposed at the halfway position of the introduction tube 19a. In addition, a supply tube 19c of the ACD solution storage bag 16B is connected to the introduction tube 19a. A pump 32b suctioning the ACD solution from the ADD solution storage bag 16B is disposed at the halfway position of the supply tube 19c. As a result, the collection system 10 suppresses coagulation of the whole blood by supplying the ACD solution to the introduction tube 19a.

After the whole blood flows into the first chamber 44 from one end portion to which the introduction tube 19a is connected, the whole blood flows in a circumferential direction through the outer periphery of the conduit housing 38 along the belt shape of the primary separation bag 16A and heads for the other end portion. Then, the whole blood is subjected to centrifugal separation during the flow by receiving the centrifugal force that results from the rotation of the rotor 24 (conduit housing 38).

Figure 2:
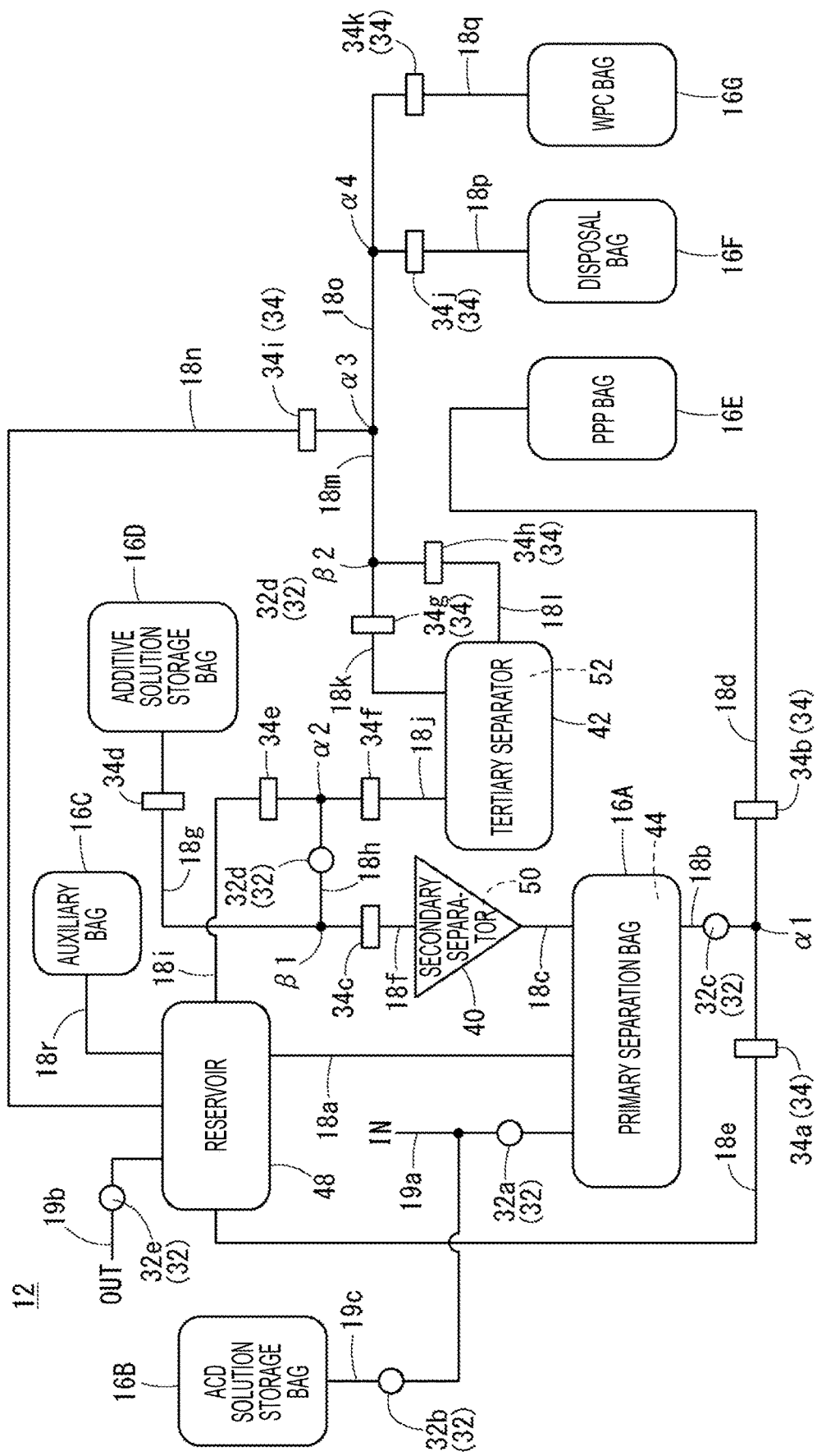
FIG. 2 is a block diagram schematically illustrating a circuit configuration example of a blood sampling circuit set illustrated in FIG. 1.

As illustrated in FIGS. 1 and 2, first to third tubes 18a to 18c are connected to the other end portion side of the primary separation bag 16A. The first tube 18a is connected to the lower side of the other end portion of the primary separation bag 16A and is connected to a reservoir 48 disposed in the cassette 20 through the inside of the bundle tube 46. The first tube 18a allows concentrated erythrocytes (remaining component) generated by the centrifugal separation in the first chamber 44 to flow out to the reservoir 48.

The second tube 18b is connected to the upper side of the other end portion of the primary separation bag 16A. The second tube 18b branches into a fourth tube 18d connected to the PPP bag 16E and a fifth tube 18e connected to the reservoir 48 at a branch point α1 through a predetermined path in the bundle tube 46 and the cassette 20. A pump 32c is disposed at the halfway position of the second tube 18b, and the pump 32c allows a plasma component (platelet poor plasma) generated by the centrifugal separation of the whole blood to flow out or flow in. In addition, a clamp 34b is disposed on the fourth tube 18d and a clamp 34a is disposed on the fifth tube 18e.

The third tube 18c is connected to the up-down direction intermediate portion of the other end portion of the primary separation bag 16A. The end portion of the third tube 18c that is on the opposite side is connected to the secondary separator 40 in the conduit housing 38. The third tube 18c allows a buffy coat (first blood component) generated by the centrifugal separation of the whole blood to flow out. The buffy coat includes a leukocyte component and platelet rich plasma (platelet-containing component). In other words, the buffy coat has a large number of platelets.

Figure 3:
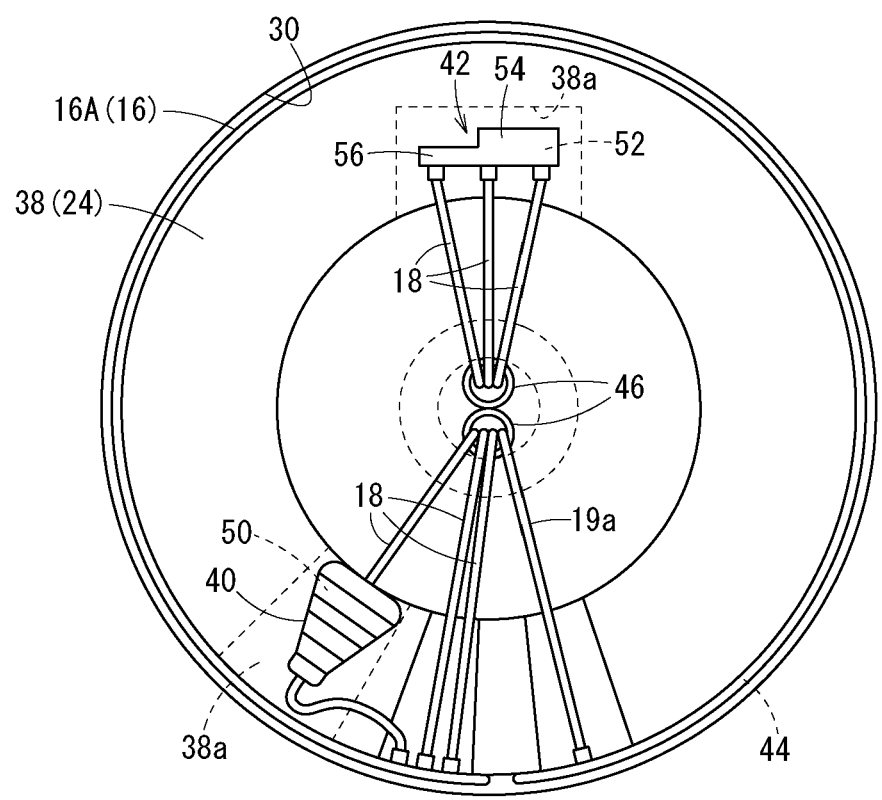
FIG. 3 is a plan view illustrating an example of arrangement of a primary separation bag, a secondary separator, and a tertiary separator of the blood sampling circuit set illustrated in FIG. 1.

The secondary separator 40 has a second chamber 50 temporarily accommodating the buffy coat and performs further centrifugal separation on the buffy coat by the centrifugal force being applied from the conduit housing 38. The secondary separator 40 is formed in a conical shape. In a state where the conduit housing 38 is attached, a top portion of the secondary separator 40 is arranged on a side far from the centrifugal center and a bottom surface of the secondary separator 40 is arranged on a side close to the centrifugal center as illustrated in FIG. 3. The third tube 18c is connected to the top portion of the secondary separator 40, and a sixth tube 18f (first flow path portion) is connected to the bottom surface of the secondary separator 40. In addition, the secondary separator 40 has a plurality of steps on a tapered side surface. Accordingly, once the buffy coat is subjected to the centrifugal separation, the leukocyte component (second blood component) with a heavy specific gravity is caught in each step and a platelet-containing component 100 (refer also to FIG. 8B) including platelets and plasma with a light specific gravity is brought to the centrifugal center. Then, the platelet-containing component 100 is allowed to flow out from the sixth tube 18f.

The sixth tube 18f is connected to the cassette 20 through the inside of the bundle tube 46 from the secondary separator 40, is merged with a seventh tube 18g (second flow path portion) at a merging point β1 in the cassette 20, and is connected to an eighth tube 18h. A clamp 34c (first clamp) is disposed at the halfway position of the sixth tube 18f. The seventh tube 18g leads to the additive solution storage bag 16D, and a clamp 34d (second clamp) is disposed at the halfway position of the seventh tube 18g. The eighth tube 18h extends between the merging point β1 and a branch point α2 and is provided with a pump 32d at the halfway position of the eighth tube 18h. Then, the eighth tube 18h branches into a ninth tube 18i connected to the reservoir 48 and a tenth tube 18j connected to the tertiary separator 42 at the branch point α2. In addition, a clamp 34e is disposed on the ninth tube 18i and a clamp 34f is disposed on the tenth tube 18j.

The end portion of the tenth tube 18j that is on the side opposite to the branch point α2 is connected to an inflow port 77 of the tertiary separator 42. The tertiary separator 42 has a third chamber 52 accommodated in the conduit housing 38 and temporarily storing the platelet-containing component 100 flowing in from the sixth tube 18f and the platelet additive solution 102 flowing in from the seventh tube 18g. The tertiary separator 42 separates the platelet-containing component 100 into plasma (another component) and platelets by the centrifugal force being applied. The configuration of the tertiary separator 42 will be described in detail later. Two tubes (eleventh and twelfth tubes 18k and 18l) extending into the cassette 20 through the bundle tube 46 are connected to the tertiary separator 42.

The eleventh tube 18k is a tube through which mainly plasma flows out from the tertiary separator 42, and the twelfth tube 18l is a tube through which mainly platelets flow out from the tertiary separator 42. Clamps 34g and 34h are disposed on the eleventh and twelfth tubes 18k and 18l, respectively. In addition, the eleventh and twelfth tubes 18k and 18l have end portions merged with each other at a merging point β2 and connected to a thirteenth tube 18m. The thirteenth tube 18m is divided into a fourteenth tube 18n connected to the reservoir 48 and a fifteenth tube 18o at a branch point α3 downstream of the thirteenth tube 18m. A clamp 34i is disposed on the fourteenth tube 18n. Furthermore, the fifteenth tube 18o is divided into a sixteenth tube 18p connected to the disposal bag 16F and a seventeenth tube 18q connected to the WPC bag 16G at a branch point α4. Clamps 34j and 34k are disposed on the sixteenth and seventeenth tubes 18p and 18q, respectively.

In addition, the reservoir 48 disposed in the cassette 20 temporarily stores the blood components returned to the donor. An eighteenth tube 18r connected to the auxiliary bag 16C and a delivery tube 19b connected to the blood inlet-outlet portion of the donor as well as the first, fifth, ninth, and fourteenth tubes 18a, 18e, 18i, and 18n are connected to the reservoir 48. The introduction tube 19a, the delivery tube 19b, and the supply tube 19c are connected to the cassette 20 as a triple tube. A pump 32e for allowing the blood components returned to the donor to flow is disposed at the halfway position of the delivery tube 19b. Although the present embodiment is configured such that the introduction tube 19a and the delivery tube 19b are connected to the single indwelling needle in the blood inlet-outlet portion and blood sampling and blood returning are performed with the same needle, the collection system 10 may also be configured such that the blood sampling and the blood returning are performed on separate paths by two or more needles being used.

The blood sampling circuit set 12 is configured as described above by being attached to the centrifugal separation device 14. The blood sampling circuit set 12 performs the centrifugal separation of the whole blood of the donor by the conduit housing 38, the pump 32, and the clamp 34 being operated at an appropriate timing when the centrifugal separation device 14 is driven.

Next, the configuration of the tertiary separator 42 described above will be described in detail. As illustrated in FIG. 3, the tertiary separator 42 is fixedly arranged in the cavity portion 38a formed near the inside of the conduit housing 38. As a result, a centrifugal force weaker than the centrifugal force that is applied to the primary separation bag 16A and the secondary separator 40 is applied to the tertiary separator 42 as the conduit housing 38 rotates. In addition, the centrifugal separation device 14 has the tertiary separator 42 arranged at the position on the side opposite to both end portions of the primary separation bag 16A attached to the conduit housing 38 across the centrifugal center so that the rotation of the conduit housing 38 is stabilized during the centrifugal separation. The arrangement position of the tertiary separator 42 may be designed freely. For example, the tertiary separator 42 may be put in the vicinity of the arrangement position of the secondary separator 40.

Figure 4:
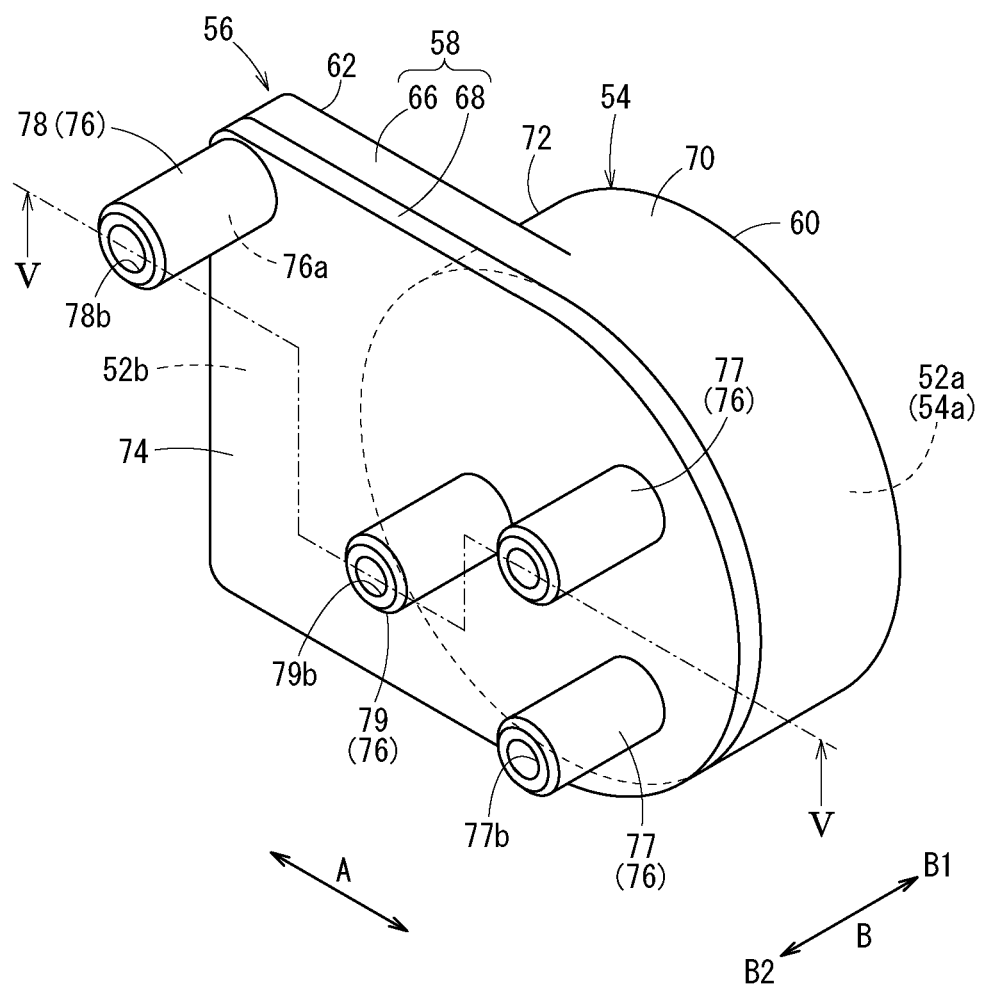
FIG. 4 is a perspective view illustrating the tertiary separator illustrated in FIG. 1.
Figure 5:
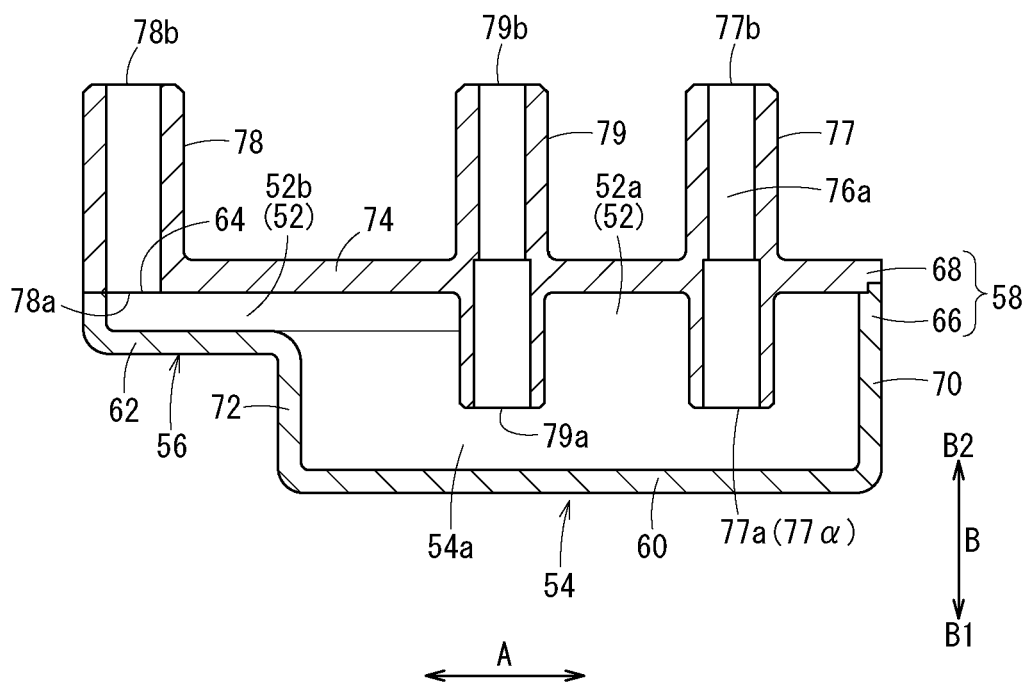
FIG. 5 is a cross-sectional view taken along line V-V of FIG. 4.

As illustrated in FIGS. 4 and 5, a container 58 (main body portion) capable of storing the platelet-containing component 100 and the platelet additive solution 102 constitutes the tertiary separator 42. In front view as seen from the centrifugal center, the container 58 is formed in a substantially rectangular shape. In addition, the container 58 has a first region 54 that extends to one side from the middle portion thereof in a longitudinal direction (arrow A direction) and is thick in a centrifugal direction (arrow B1 direction) in plan view and a second region 56 that extends to the other side in the longitudinal direction and is thin in the centrifugal direction in plan view. The first region 54 and the second region 56 have widths in a short direction set to be equal to each other and are continuous to each other. In front view, one side of the first region 54 in the longitudinal direction is formed on a side that has a round corner which has a large radius of curvature. In front view, the other side of the second region 56 in the longitudinal direction is formed on a side that has a round corner which has a small radius of curvature.

The first region 54 has a first bottom portion 60 that is significantly away from a ceiling portion 74 on the centrifugal center side toward the centrifugal direction, and thus a first space 52a that has a large volume is built on the inside thereof. The second region 56 has a second bottom portion 62 that is slightly away from the ceiling portion 74 toward the centrifugal direction, and thus a second space 52b that has a small volume is built on the inside thereof. In other words, the first bottom portion 60 is at a position that is more away from the centrifugal center than the position of the second bottom portion 62. The ceiling portions 74 of the first region 54 and the second region 56 are flush with and continuous to each other. The first space 52a and the second space 52b constitute the third chamber 52 by communicating with each other in the longitudinal direction.

In addition, the container 58 is configured to be capable of being divided into a vessel portion 66 that has the third chamber 52 described above and has an opening portion 64 of the third chamber 52 in the direction (anti-centrifugal direction: arrow B2 direction) opposite to the centrifugal direction and a lid portion 68 attached to the opening portion 64 of the vessel portion 66.

The vessel portion 66 has the first and second bottom portions 60 and 62 described above and a side wall 70 protruding from each of the bottom portions 60 and 62 toward the anti-centrifugal direction. The side wall 70 forms the third chamber 52 by surrounding the first and second bottom portions 60 and 62 in a circumferential direction. In addition, the vessel portion 66 has a step wall 72 on the boundary between the first bottom portion 60 and the second bottom portion 62 because the depths (heights) of the first bottom portion 60 and the second bottom portion 62 differ from each other.

In front view, the step wall 72 is shaped such that the up-down direction middle portion thereof is recessed toward the second region 56 side. An accommodating portion 54a accommodating (accumulating) platelets as centrifugal separation proceeds is configured inside the first bottom portion 60, the step wall 72, and the side wall 70 that is up to the same height as the step wall 72 from the first bottom portion 60. In other words, the accommodating portion 54a is a space set at the part of the first space 52a that is near the first bottom portion 60 (on the arrow B1 direction side).

In the cross-sectional view that is illustrated in FIG. 5, the step wall 72 is formed as a wall orthogonal to the first and second bottom portions 60 and 62, and thus the platelets are accumulated with greater ease. Furthermore, it is preferable that the height of the step wall 72 (distance in the anti-centrifugal direction from the first bottom portion 60 to the second bottom portion 62) is set to be equal to or greater than the height of the separation boundary surface at a time when the platelet-containing component 100 is separated into platelets and plasma as a result of centrifugal separation. As a result, an overflow of platelets from the step wall 72 can be significantly suppressed, and thus an outflow of platelets from the third chamber 52 can be suppressed and plasma can be discharged in a more reliable manner.

The lid portion 68 has the ceiling portion 74 that has a flat plate shape corresponding to the front shape of the side wall 70 of the vessel portion 66, and the ceiling portion 74 closes the opening portion 64 of the vessel portion 66 by appropriate attachment means such as adhesion. A plurality of attachment ports 76 for attaching the tubes 18 connected to the tertiary separator 42 is disposed in the ceiling portion 74 of the lid portion 68.

The plurality of attachment ports 76 is formed in a tubular shape and extends in the direction (arrow B direction) that is orthogonal to the plane direction of the ceiling portion 74. A communication passage 76a is formed along an axial direction through the axial center portion of each attachment port 76. The diameters of the communication passages 76a of the attachment ports 76 may be set to be equal to each other or may differ from each other depending on fluids scheduled to flow. Each attachment port 76 is composed of a pair of the inflow ports 77, an outflow port 78, and a recovery port 79.

The pair of inflow ports 77 allows the platelet-containing component 100 and the platelet additive solution 102 to flow into the third chamber 52 by the tenth tube 18j of the blood sampling circuit set 12 being connected to the pair of inflow ports 77. In other words, the tenth tube 18j bifurcates at the halfway position that reaches the tertiary separator 42 from the branch point α2 in FIG. 2 and the branch tubes are mounted at the pair of inflow ports 77, respectively.

The blood sampling circuit set 12 is capable of constituting various circuits as well as the above-described circuit allowing the platelet-containing component 100 and the platelet additive solution 102 to flow in from the common inflow ports 77. In an alternative configuration, for example, the platelet-containing component 100 and the platelet additive solution 102 may be allowed to separately flow in by the sixth tube 18f being connected to one of the inflow ports 77 and the seventh tube 18g being connected to the other inflow port 77. In addition, it is a matter of course that one or three or more inflow ports 77 may be disposed.

As illustrated in FIG. 4, the pair of inflow ports 77 is formed near one side of the first region 54 in the longitudinal direction and at positions separated from each other in the short direction. In addition, as illustrated in FIG. 5, each inflow port 77 protrudes in the centrifugal direction and the anti-centrifugal direction (arrow B2 direction) from the ceiling portion 74 as a base point. The protruding end of each inflow port 77 that protrudes in the centrifugal direction is arranged close to the first bottom portion 60 of the third chamber 52 (in the accommodating portion 54a) and has an inflow portion 77a allowing the communication passage 76a and the third chamber 52 to communicate with each other. In this case, two openings 77a of the pair of inflow ports 77 constitute the inflow portion 77a. The inflow portion 77a may also be composed of one or three or more openings 77a.

In plan view, the openings 77a are arranged in the first space 52a (accommodating portion 54a). An opening 77b allowing a fluid in the tenth tube 18j to flow into the communication passage 76a is disposed at the protruding end of each inflow port 77 that protrudes in the anti-centrifugal direction.

The outflow port 78 allows mainly plasma 106 and the platelet additive solution 102 to flow out from the third chamber 52 by the eleventh tube 18k of the blood sampling circuit set 12 being connected to the outflow port 78. In front view, the outflow port 78 is disposed at a position in close proximity to an upper side corner portion of the second region 56. In addition, the outflow port 78 protrudes in the anti-centrifugal direction from the ceiling portion 74 and does not protrude in the centrifugal direction from the ceiling portion 74. An opening 78a (outflow portion) allowing a fluid to flow out to the communication passage 76a of the outflow port 78 is disposed on the surface of the ceiling portion 74 that is opposite to the place where the outflow port 78 is formed. In other words, the opening 78a is arranged in the second region 56 in plan view. The outflow portion is not limited to the single opening 78a and may also be composed of two or more openings 78a (outflow ports 78). An opening 78b allowing the fluid in the communication passage 76a to flow out to the eleventh tube 18k is disposed at the protruding end of the outflow port 78 that protrudes in the anti-centrifugal direction.

The recovery port 79 allows washed platelets and the platelet additive solution 102 to flow out from the third chamber 52 by the twelfth tube 18l of the blood sampling circuit set 12 being connected to the recovery port 79. The recovery port 79 is formed in the longitudinal direction middle portion (first region 54) and the up-down direction middle portion of the ceiling portion 74. As is the case with the inflow port 77, the recovery port 79 protrudes from the ceiling portion 74 in the centrifugal direction and the anti-centrifugal direction alike. An opening 79a (recovery unit) allowing a fluid in the third chamber 52 to flow into the communication passage 76a is disposed at the protruding end of the recovery port 79 that protrudes in the centrifugal direction. In other words, the opening 79a is arranged at a position more away from the centrifugal center than the opening 78a of the outflow port 78 (position substantially equivalent to the opening 77a). The recovery unit is not limited to the single opening 79a and may be composed of two or more openings 79a (recovery ports 79) as well. An opening 79b allowing the fluid in the communication passage 76a to flow out to the twelfth tube 18l is disposed at the protruding end of the recovery port 79 that protrudes in the anti-centrifugal direction.

The tertiary separator 42 is not limited to the configuration described above and various application examples and modification examples can be adopted for the tertiary separator 42. For example, the tertiary separator 42 may have two or more outflow ports 78 and recovery ports 79 disposed therein or the inflow port 77, the outflow port 78, or the recovery port 79 may be disposed in the vessel portion 66. Furthermore, the tertiary separator 42 may be configured such that the platelet-containing component 100 and the platelet additive solution 102 are supplied to the vicinity of the longitudinal direction middle portion thereof by the installation positions of the inflow port 77 and the recovery port 79 in a width direction being exchanged with each other.

In addition, for example, the tertiary separator 42 may be configured to have a flush bottom portion (accommodating portion 54a) sufficiently away from the opening 78a of the outflow port 78 toward the centrifugal direction without being provided with the first bottom portion 60 and the second bottom portion 62 that have different heights. In other words, the tertiary separator 42 may be capable of allowing plasma to flow out after centrifugal separation into platelets and the plasma is performed in the third chamber 52, and the shape thereof and the position of the opening of the port are not particularly limited. The first and second bottom portions 60 and 62 may also be formed in a recessed shape, a protruding shape, and so on without being formed in a flat shape in sectional plan view.

Basically, the collection system 10 according to the present embodiment is configured as described above. The action and effect thereof will be described below.

While preparing the collection system 10, a medical professional such as a doctor and a nurse attaches the blood sampling circuit set 12 to the centrifugal separation device 14 with the tubes 18 appropriately wired to the cassette 20. At this time, the medical professional winds the primary separation bag 16A around the outer peripheral surface of the conduit housing 38 and accommodates the rotor 24 in the accommodating space 30 of the centrifugal separation device 14. In addition, the medical professional mounts the cassette 20 in the attachment portion 28 of the centrifugal separation device 14 and hangs the other bags 16B to 16G on a stand (not illustrated) or the like. As a result of the mounting of the cassette 20, the clamps 34, the pumps 32, and the sensors are arranged at predetermined positions of the tubes 18.

Figure 6:
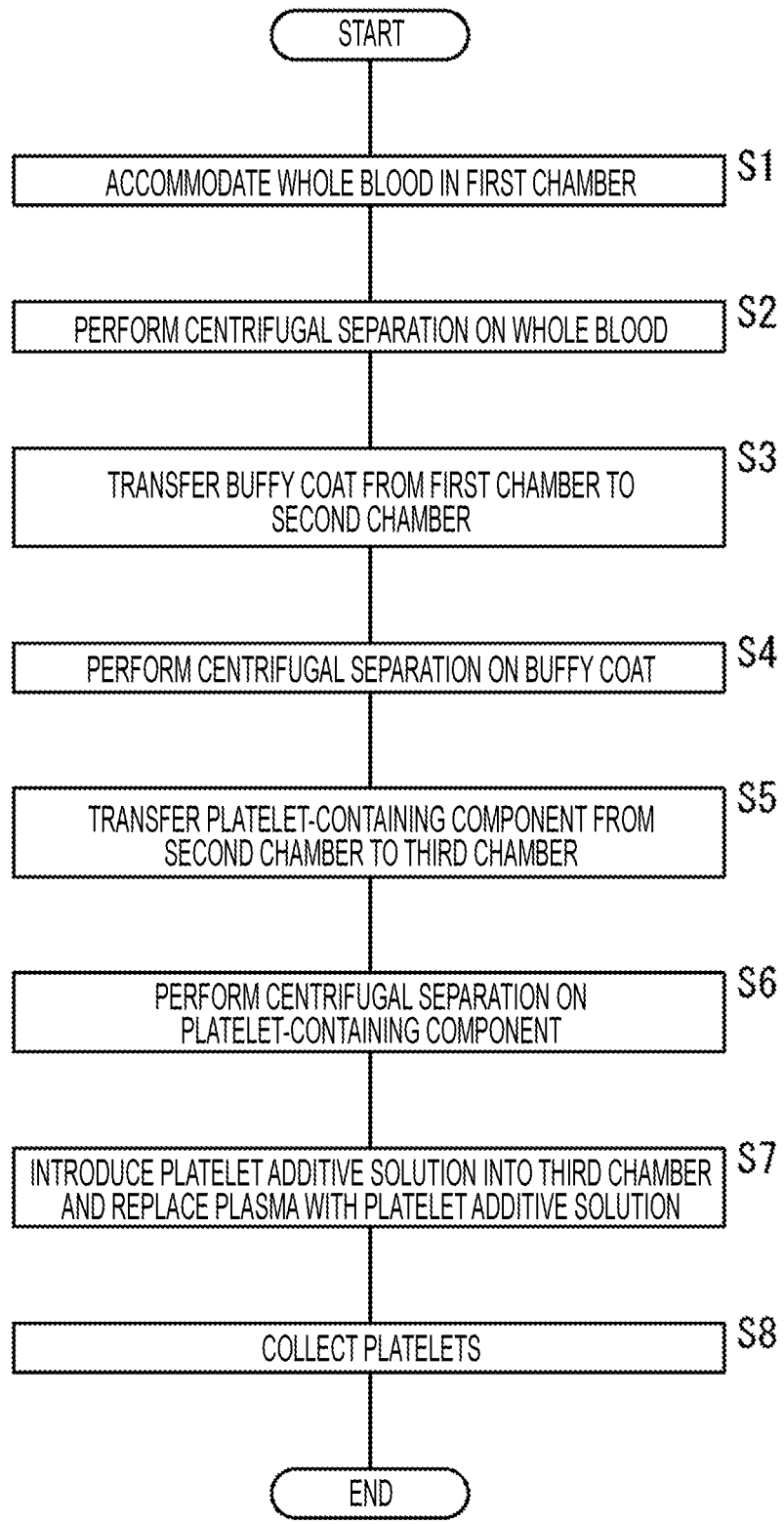
FIG. 6 is a flowchart of a platelet collection method based on the blood sampling system illustrated in FIG. 1.

During component blood sampling, the medical professional first punctures the donor with the indwelling needle and builds the blood inlet-outlet portion by connecting connectors of the introduction tube 19a and the delivery tube 19b of the blood sampling circuit set 12 to the indwelling needle. Then, an operation of the collection system 10 is initiated. The collection system 10 collects platelets by performing extracorporeal blood component treatment along the procedure of the flowchart that is illustrated in FIG. 6 based on control by a control unit (not illustrated) disposed in the centrifugal separation device 14.

In this case, the collection system 10 accommodates the whole blood of the donor in the first chamber 44 of the primary separation bag 16A (Step S1) and performs centrifugal separation on the whole blood by rotating the primary separation bag 16A (Step S2). Next, the buffy coat that is separated by the whole blood being subjected to the centrifugal separation is transferred from the first chamber 44 to the second chamber 50 of the secondary separator 40 (Step S3) and the buffy coat is subjected to centrifugal separation by the secondary separator 40 being rotated (Step S4). Next, the platelet-containing component 100 that is separated by the buffy coat being subjected to the centrifugal separation is transferred from the second chamber 50 to the third chamber 52 of the tertiary separator 42 (Step S5) and the platelet-containing component 100 is subjected to centrifugal separation by the tertiary separator 42 being rotated (Step S6). Furthermore, the platelet additive solution 102 is introduced into the third chamber 52 and the plasma that is separated by the platelet-containing component 100 being subjected to the centrifugal separation is replaced with the platelet additive solution 102 (Step S7). Then, the platelets that remain in the third chamber 52 are collected along with the platelet additive solution 102 (Step S8). This platelet collection method will be described in further detail below.

Figure 7:
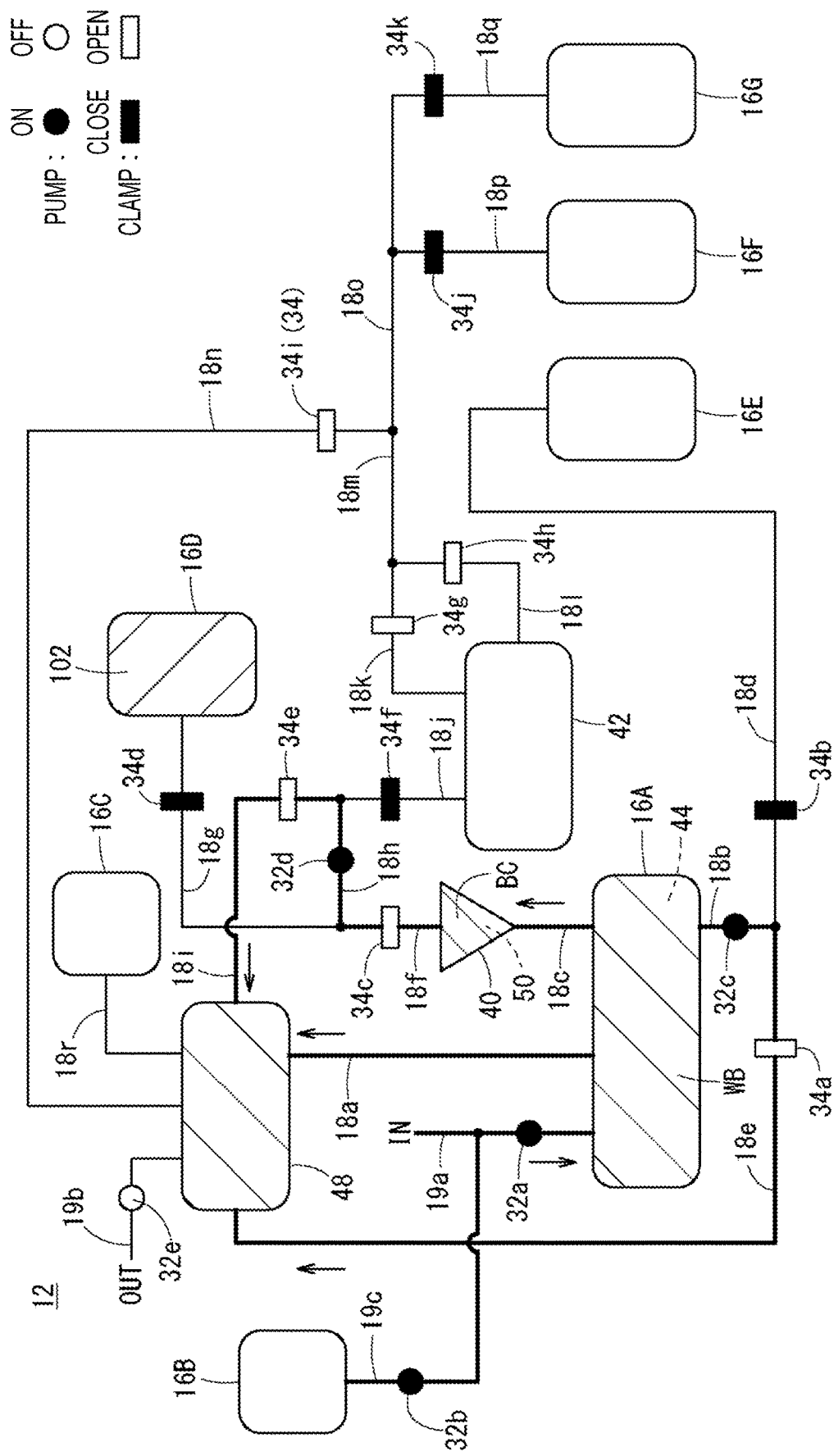
FIG. 7 is a first explanatory diagram illustrating an operation of the blood sampling circuit set during component blood sampling.

As illustrated in FIG. 7, the collection system 10 suctions whole blood WB from the blood inlet-outlet portion formed in the donor by driving the pump 32a of the introduction tube 19a and allows the whole blood WB to flow into the first chamber 44 of the primary separation bag 16A in Step S1. Preferably, the flow velocity of the whole blood WB is, for example, 60 mL/min to 120 mL/min. At this time, coagulation of the whole blood WB is suppressed by the pump 32b being driven and the ACD solution being supplied from the ACD solution storage bag 16B. The whole blood WB is continuously supplied to the first chamber 44 and flows from one end side of the belt shape to which the introduction tube 19a is connected toward the other end side (refer also to FIG. 1).

During this flow, the centrifugal separation device 14 executes Step S2. In other words, a centrifugal force is applied to the primary separation bag 16A by the rotor 24 being rotated at a predetermined rotation speed. As a result, the whole blood WB is separated into concentrated erythrocytes, platelet poor plasma, and a buffy coat BC depending on the specific gravities of the components when the whole blood WB flows to the other end side.

In Step S3, the centrifugal separation device 14 allows the buffy coat BC to flow to the secondary separator 40 via the third tube 18c by driving the pump 32d. In addition, the centrifugal separation device 14 allows the concentrated erythrocytes to flow to the reservoir 48 via the first tube 18a. Furthermore, the centrifugal separation device 14 allows the platelet poor plasma to flow to the reservoir 48 via the second and fifth tubes 18b and 18e by driving the pump 32c, opening the clamp 34a, and closing the clamp 34b.

The secondary separator 40 executes Step S4 by a centrifugal force being applied as the conduit housing 38 rotates. In other words, the buffy coat BC is subjected to centrifugal separation in the second chamber 50 and separated into leukocytes and the platelet-containing component 100. Then, the centrifugal separation device 14 allows the platelet-containing component 100 to temporarily flow to the reservoir 48 by opening the clamps 34c and 34e and closing the clamps 34d and 34f.

Figure 8A:
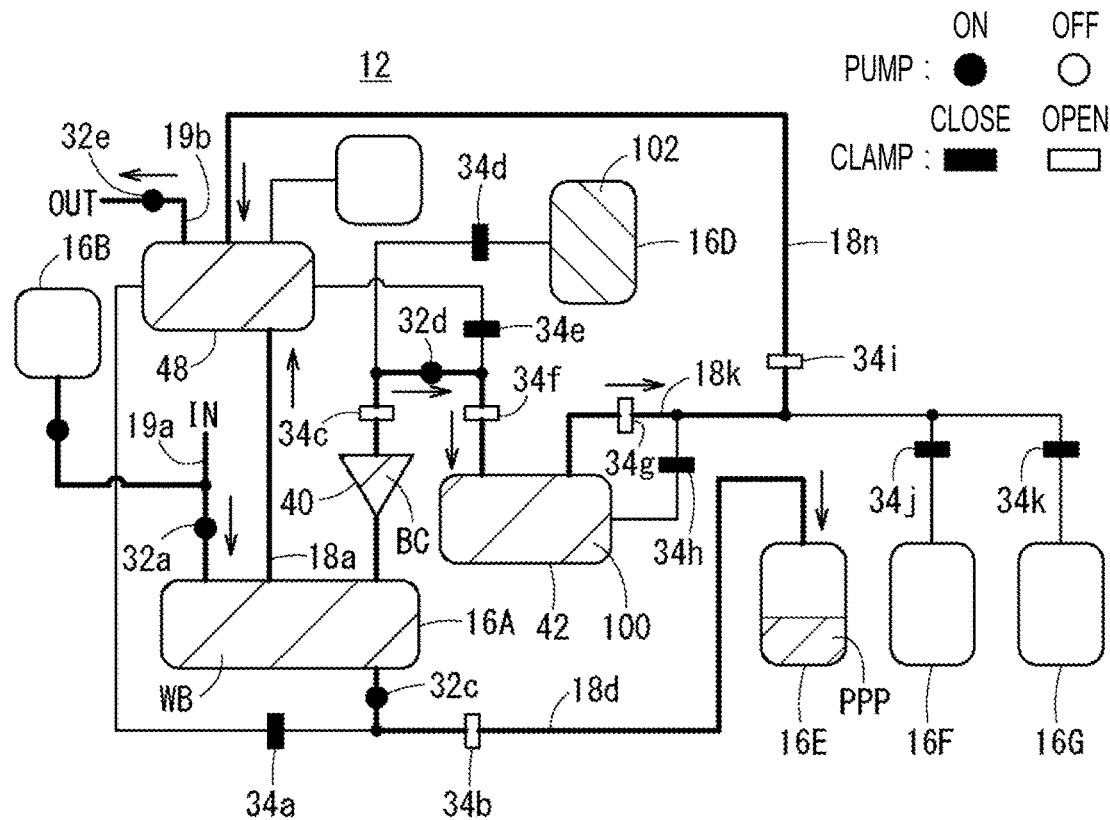
FIG. 8A is a second explanatory diagram illustrating the operation of the blood sampling circuit set leading from FIG. 7.

Subsequently, the centrifugal separation device 14 executes Step S5. In other words, the centrifugal separation device 14 allows the platelet-containing component 100 to flow from the secondary separator 40 to the tertiary separator 42 by closing the clamp 34e and opening the clamp 34f as illustrated in FIG. 8A. At this time, a flow of the platelet additive solution 102 is regulated by the clamp 34d remaining closed. In addition, the centrifugal separation device 14 stores the platelet poor plasma in the PPP bag 16E by closing the clamp 34a and opening the clamp 34b.

Figure 8B:
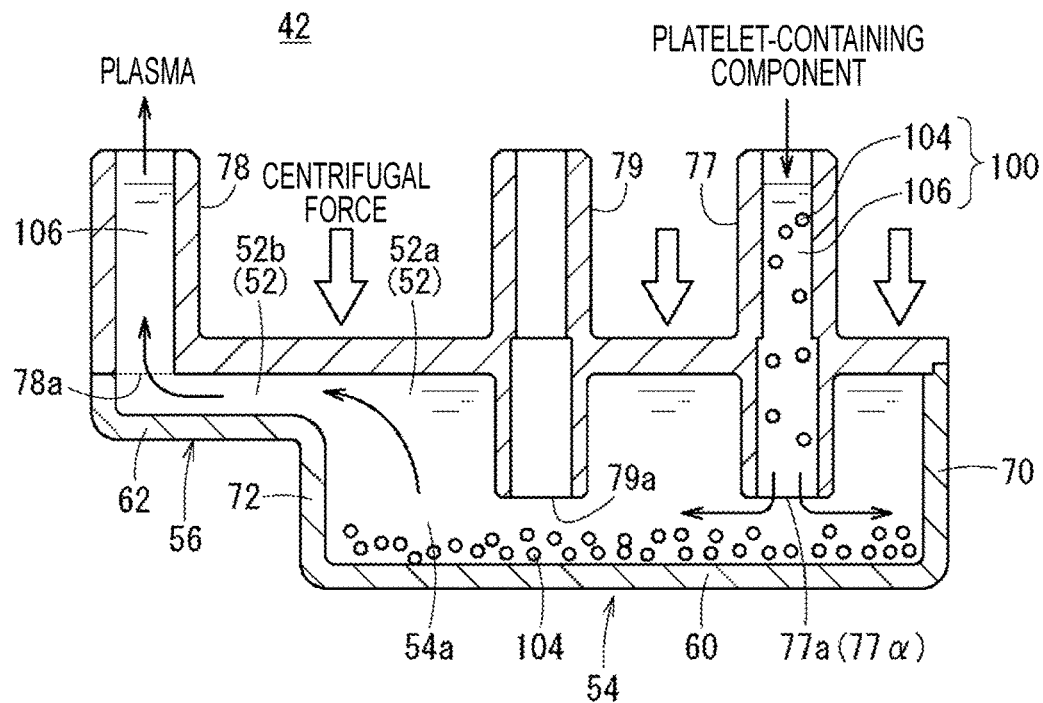
FIG. 8B is a cross-sectional view schematically illustrating the state of the tertiary separator in FIG. 8A.

As Step S5 is initiated, the platelet-containing component 100 flows into the tertiary separator 42 via the sixth, eighth, and tenth tubes 18f, 18h, and 18j (refer to FIG. 8B). The opening 77a of the inflow port 77 is in close proximity to the first bottom portion 60, and thus the platelet-containing component 100 is supplied to the first space 52a from a position close to the first bottom portion 60. In addition, since a plurality of the openings 77a of the inflow ports 77 is disposed in the container 58, an equal inflow of the platelet-containing component 100 is performed without the platelet-containing component 100 concentrating on one place.

Then, the centrifugal separation device 14 executes Step S6 by the centrifugal force being applied as the conduit housing 38 rotates. In other words, the platelet-containing component 100 is subjected to centrifugal separation in the first space 52a of the third chamber 52 and separated into platelets 104 and the plasma 106. At this time, the platelets 104 move more in the centrifugal direction (that is, to the accommodating portion 54a of the first space 52a) than the plasma 106. Then, a movement of the platelets 104 to the second space 52b side is suppressed by the step wall 72. The plasma 106, in contrast, gathers in the anti-centrifugal direction and easily flows from the first space 52a to the second space 52b as the platelet-containing component 100 continuously flows in. Then, the plasma 106 flows into the opening 78a of the outflow port 78 and flows to the outside of the tertiary separator 42. Accordingly, the platelets 104 are gradually accumulated and concentrated in the accommodating portion 54a.

As illustrated in FIG. 8A, the centrifugal separation device 14 guides the plasma 106 flowing out from the outflow port 78 to the reservoir 48 by opening the clamps 34g and 34i and closing the clamp 34h. The blood components stored in the reservoir 48 (such as the concentrated erythrocytes and the plasma) flow and return to the blood inlet-outlet portion of the donor via the delivery tube 19b under the driving of the pump 32e. Then, the centrifugal separation device 14 maintains the states that are illustrated in FIGS. 8A and 8B (that is, continues to execute Steps S1 to S6) until the platelet poor plasma is sufficiently stored in the PPP bag 16E. Once the storage in the PPP bag 16E is over, the platelet poor plasma is allowed to flow to the reservoir 48 by the clamp 34b being closed and the clamp 34a being opened (refer to FIG. 9A).

Figure 9A:
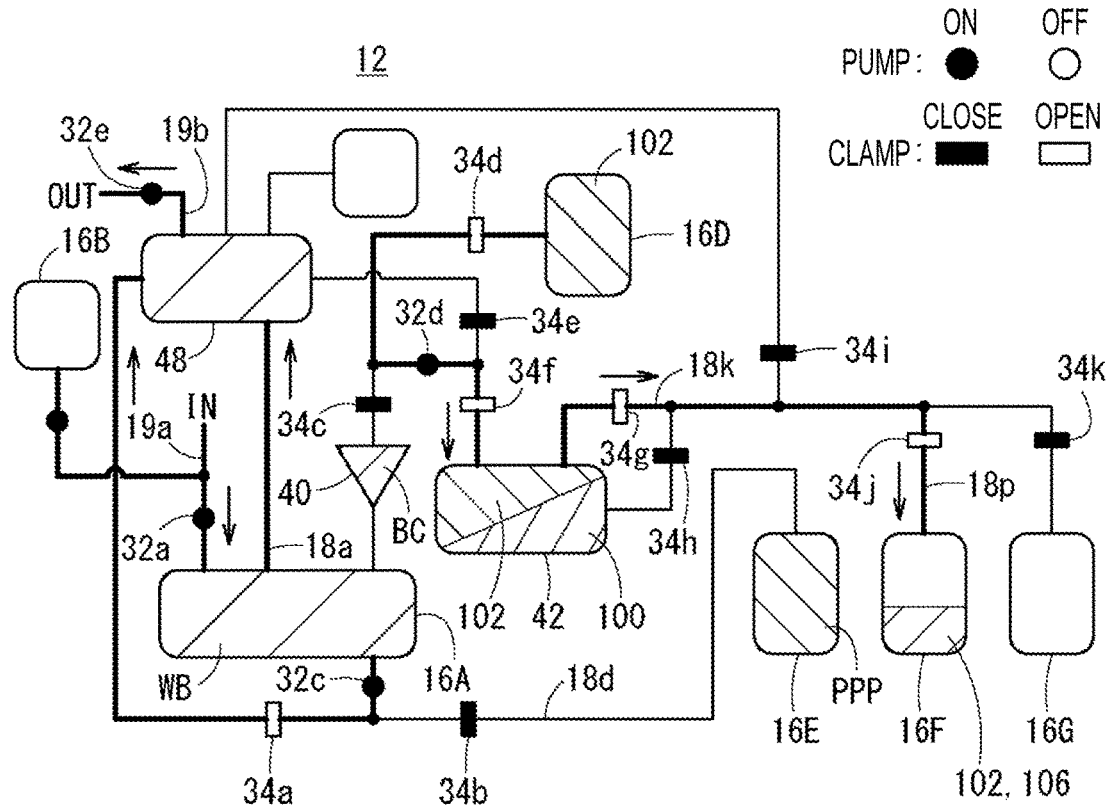
FIG. 9A is a third explanatory diagram illustrating the operation of the blood sampling circuit set leading from FIG. 8A.

After the platelets 104 are concentrated in the third chamber 52, the centrifugal separation device 14 closes the clamps 34c and 34e and opens the clamps 34d and 34f as illustrated in FIG. 9A. As a result, the centrifugal separation device 14 supplies the platelet additive solution 102 to the tertiary separator 42.

Figure 9B:
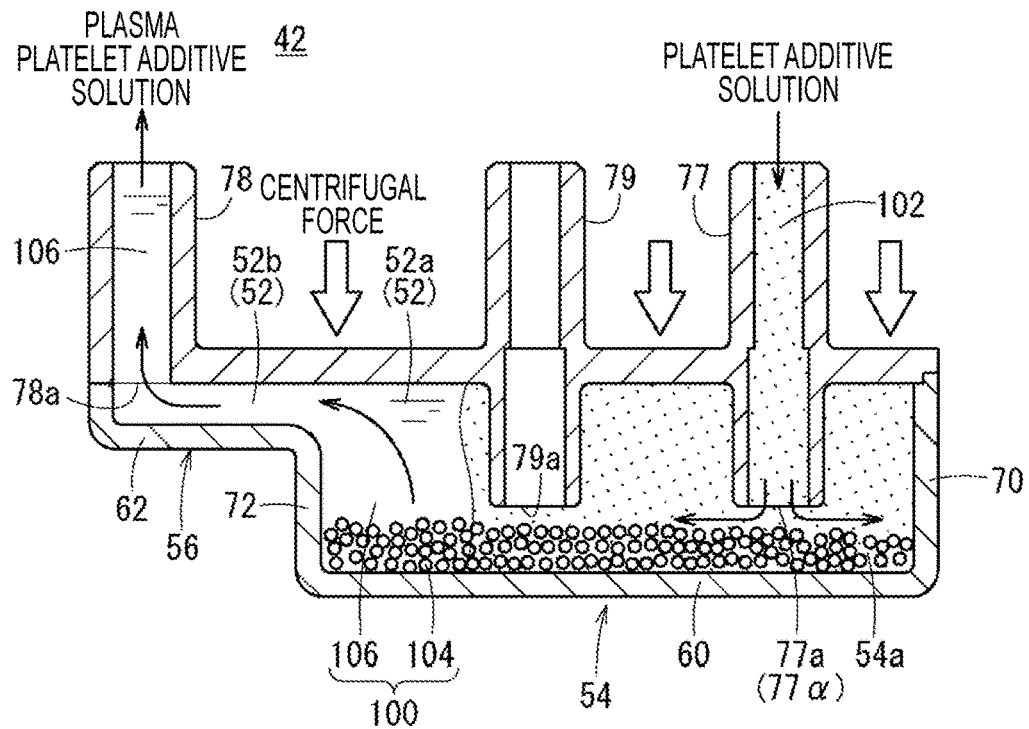
FIG. 9B is a cross-sectional view schematically illustrating the state of the tertiary separator in FIG. 9A.

In other words, the centrifugal separation device 14 executes Step S7 and allows the platelet additive solution 102 to flow into the third chamber 52 from the inflow port 77 as illustrated in FIG. 9B. The platelet additive solution 102 is lighter in specific gravity than the platelets 104, and thus moves in the anti-centrifugal direction upon receiving the centrifugal force from the conduit housing 38. Then, the platelet additive solution 102 flows to the outflow port 78 side while pushing out the plasma 106 in the third chamber 52 by being continuously supplied from the inflow port 77 and is discharged from the tertiary separator 42. Accordingly, the plasma 106 is replaced with the platelet additive solution 102 in the third chamber 52 with the platelets 104 remaining.

Referring back to FIG. 9A, the centrifugal separation device 14 closes the clamp 34i and opens the clamp 34j as the platelet additive solution 102 is supplied to the tertiary separator 42. As a result, an inflow of the platelet additive solution 102 to the donor via the reservoir 48 and the blood inlet-outlet portion is prevented by the plasma 106 and the platelet additive solution 102 flowing to the disposal bag 16F.

Figure 10A:
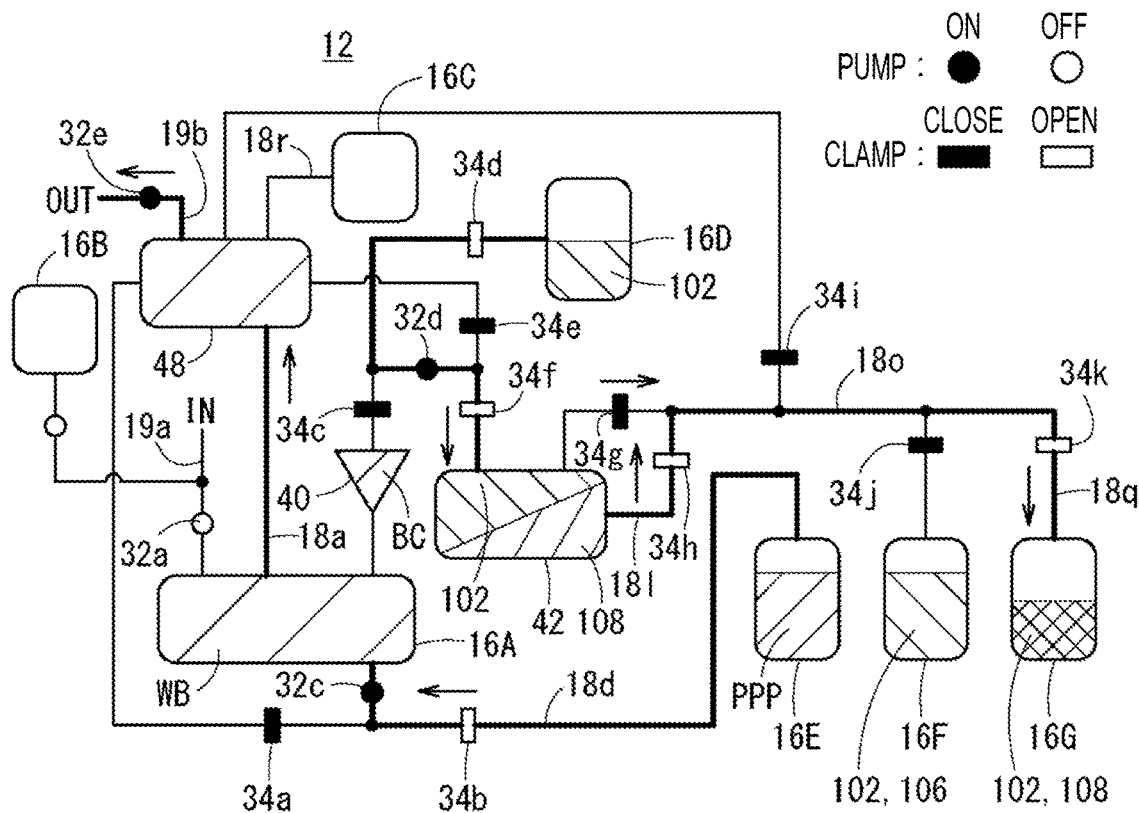
FIG. 10A is a fourth explanatory diagram illustrating the operation of the blood sampling circuit set leading from FIG. 9A.

After continuing with the state that is illustrated in FIGS. 9A and 9B to some extent, the centrifugal separation device 14 returns some of the platelet poor plasma taken into the PPP bag 16E to the primary separation bag 16A by driving the pump 32c as illustrated in FIG. 10A. Then, the platelet poor plasma is allowed to flow from the primary separation bag 16A to the reservoir 48 and the blood components are returned to the donor via the delivery tube 19b.

Subsequently, the application of the centrifugal force to the primary separation bag 16A, the secondary separator 40, and the tertiary separator 42 is stopped by the rotation of the rotor 24 being stopped. Then, the centrifugal separation device 14 intensively supplies the platelet additive solution 102 to the third chamber 52 by increasing the flow velocity (introduction speed) of the platelet additive solution 102 under the driving of the pump 32d in order to execute Step S8. For example, the introduction speed of the platelet additive solution 102 is approximately 100 mL/min in Step S8 whereas the introduction speed of the platelet additive solution 102 is approximately 5 mL/min in Step S7.

Figure 10B:
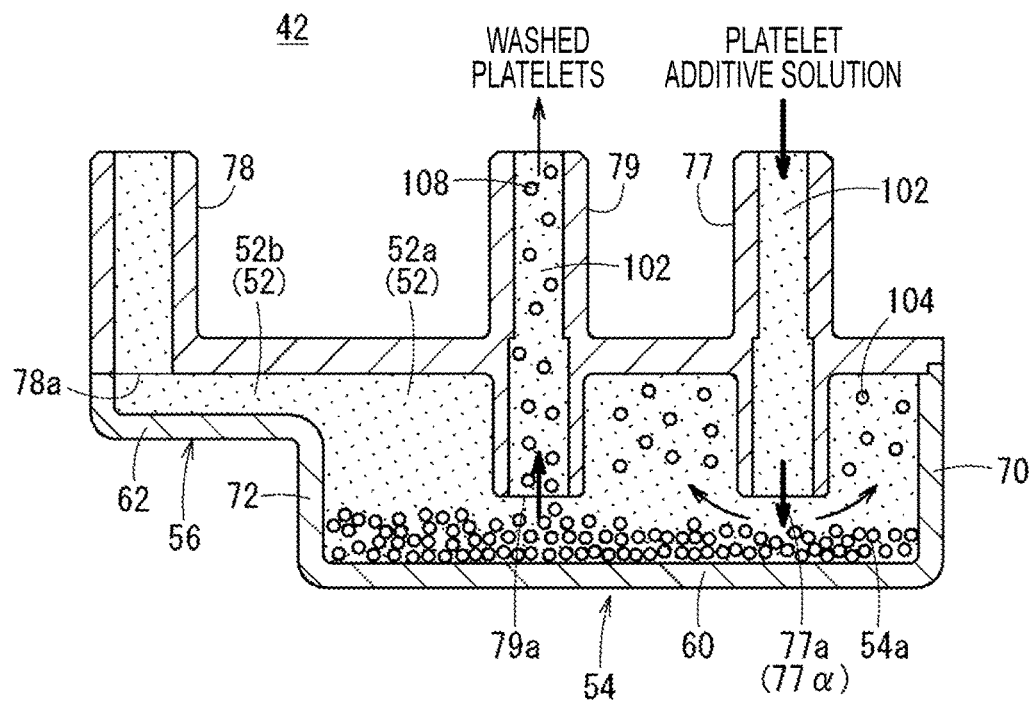
FIG. 10B is a cross-sectional view schematically illustrating the state of the tertiary separator in FIG. 10A.

As a result, the platelet additive solution 102 strongly bumps into the platelets 104 in the third chamber 52, breaks the aggregation of the platelets 104, and allows washed platelets 108 in which the platelets 104 and the platelet additive solution 102 are mixed with each other to flow out from the recovery port 79 as illustrated in FIG. 10B. At this time, an outflow of the washed platelets 108 from the outflow port 78 is prevented by the clamp 34h being open and the clamp 34g remaining closed. The washed platelets 108 have a plasma content of 5% or less since the plasma 106 is replaced with the platelet additive solution 102.

As illustrated in FIG. 10A, the washed platelets 108 are stored in the WPC bag 16G by the clamp 34j remaining closed and the clamp 34k being open. Then, the clamp 34j is closed and collection of the washed platelets 108 is terminated once the washed platelets 108 are stored by a target amount in the WPC bag 16G.

As described above, the platelet collection method and the collection system 10 according to the present embodiment allow the washed platelets 108 to be obtained by the platelet-containing component 100 transferred to the third chamber 52 being separated into the platelets 104 and the plasma 106 as a result of centrifugal separation and the plasma 106 being replaced with the platelet additive solution 102. As a result, the washed platelets 108 with a sufficiently low plasma content can be further reliably and efficiently obtained by the plasma 106 being easily removed from the platelet-containing component 100. A reduction in side effects of blood transfusion can be anticipated from the generated washed platelets 108.

In this case, a centrifugal force differing from the centrifugal force that is applied to the first and second chambers 44 and 50 is applied for the centrifugal separation in the third chamber 52 during the collection of the platelets 104, and thus the platelet-containing component 100 can be separated into the platelets 104 and the plasma 106 in a satisfactory manner. In addition, since the first chamber 44 and the second chamber 50 communicate with each other and the second chamber 50 and the third chamber 52 communicate with each other, the blood components become free to flow and the circuit that collects the platelets 104 from the whole blood WB is configured in a simple and hygienic manner. Furthermore, since the leukocytes are separated in the second chamber 50, mixing of the leukocytes with the platelet-containing component 100 supplied to the third chamber 52 can be suppressed and the washed platelets 108 including few leukocytes can be obtained.

During the centrifugal separation, the third chamber 52 of the collection system 10 allows the plasma 106 to flow out while introducing the platelet-containing component 100, and thus the platelets 104 can be concentrated in the third chamber 52 by the centrifugal separation of the platelet-containing component 100 being continuously performed. In addition, an inflow of the platelet additive solution 102 to the donor can be prevented and the plasma 106 can be returned in a satisfactory manner by the flow destination of the plasma 106 resulting from the centrifugal separation in the third chamber 52 being selectively changed. Furthermore, since the platelet additive solution 102 is allowed to flow in from the seventh tube 18g unlike the platelet-containing component 100, the inflow to the third chamber 52 can be smoothly performed and the replacement with the platelet additive solution 102 can be performed more quickly and stably.

Moreover, according to the method for collecting the platelets 104 and in the collection system 10, only the platelet additive solution 102 flows in during the introduction of the platelet additive solution 102, and thus the replacement of the separated plasma 106 with the platelet additive solution 102 is smoothly performed. At this time, the collection system 10 is capable of easily switching between the supply of the platelet-containing component 100 and the supply of the platelet additive solution 102 to the third chamber 52 by switching the opening and closing of the clamps 34c and 34d. Also, during the collection of the platelets 104, the platelets 104 aggregated in the third chamber 52 can be recovered as the washed platelets 108 while being broken by the platelet additive solution 102 by the introduction speed of the platelet additive solution 102 being increased.

Since the tertiary separator 42 for the platelets 104 and the blood sampling circuit set 12 according to the present invention have the accommodating portion 54a, the plasma 106 resulting from centrifugal separation can be brought in the anti-centrifugal direction and allowed to flow out from the opening 78a of the outflow port 78 with the platelets 104 resulting from centrifugal separation accommodated. As a result, the tertiary separator 42 is capable of recovering the washed platelets 108 with a low plasma content further reliably and efficiently from the opening 79a of the recovery port 79. At this time, the platelets 104 remain in the first bottom portion 60 in a stable manner and the plasma 106 can be allowed to flow out from the third chamber 52 in a satisfactory manner since the tertiary separator 42 has the step wall 72 between the first bottom portion 60 and the second bottom portion 62.

The tertiary separator 42 is capable of aggregating the platelets 104 in the accommodating portion 54a after the centrifugal separation since the accommodating portion 54a is disposed in the first region 54. Also, the tertiary separator 42 is capable of holding the platelets 104 in the accommodating portion 54a by performing centrifugal separation in the vicinity of the inflow of the platelet-containing component 100 since the opening 77a of the inflow port 77 is in the first region 54. Accordingly, the platelets 104 rarely flow to the second region 56 and the opening 78b of the outflow port 78 in the second region 56 allows the plasma 106 not including the platelets 104 to flow out in a satisfactory manner.

Furthermore, since the opening 79a of the recovery port 79 is arranged at the position more away from the centrifugal center than the opening 78a of the outflow port 78, the tertiary separator 42 is capable of smoothly recovering the platelets 104 (washed platelets 108) heavier in specific gravity than the plasma 106. At this time, the collection system 10 is capable of immediately storing the washed platelets 108 with a low plasma content in the WPC bag 16G along with the platelet additive solution 102.

Figure 11:
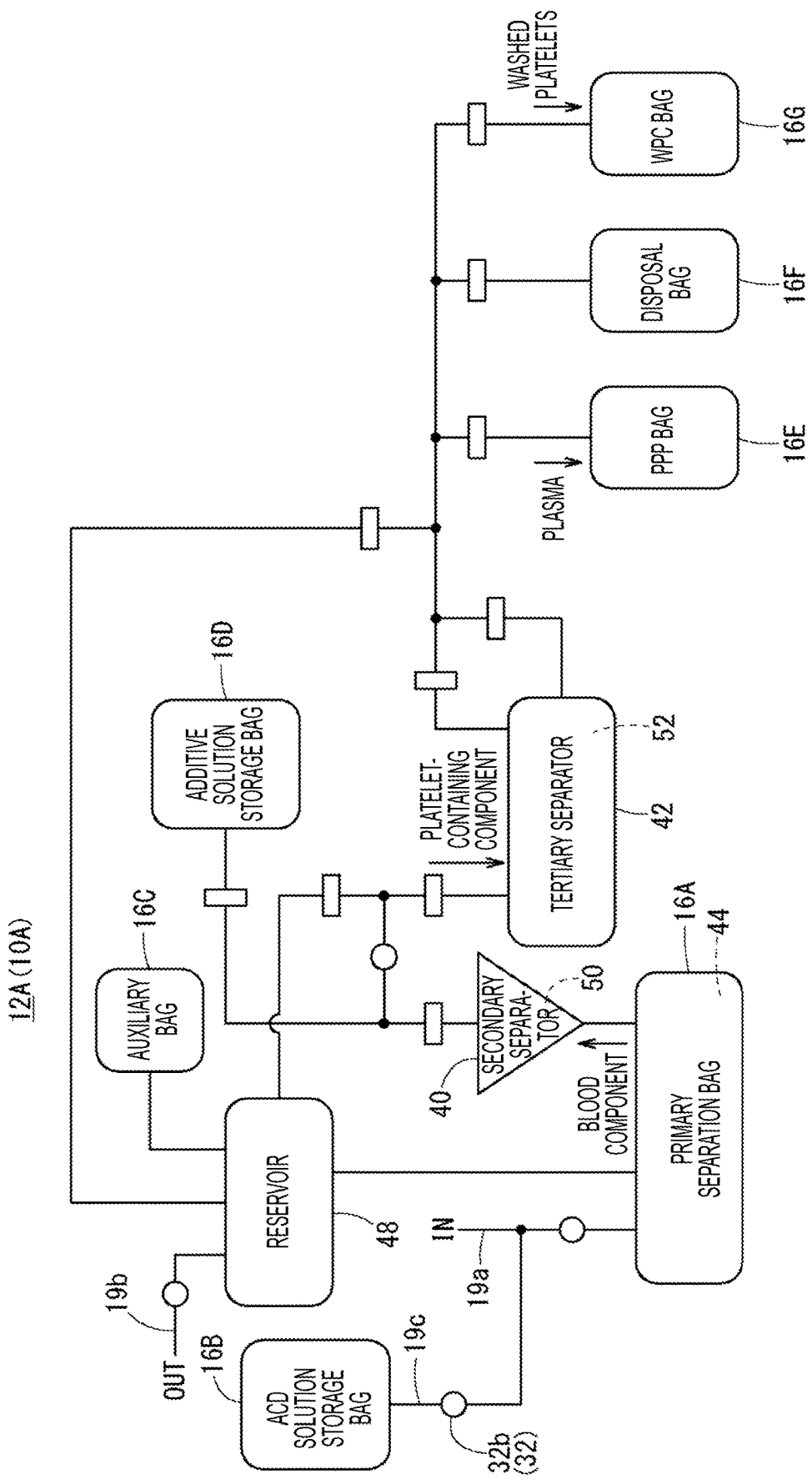
FIG. 11 is a block diagram schematically illustrating a circuit configuration example of a blood sampling system according to a modification example.

The present invention is not limited to the preferred embodiment described above. It is a matter of course that the present invention can be modified in various forms within the scope of the present invention. In an alternative configuration, for example, blood components other than concentrated erythrocytes (components including plasma, platelets, and leukocytes) may flow out to the secondary separator 40 from the primary separation bag 16A as in a collection system 10A (blood sampling circuit set 12A) according to the modification example that is illustrated in FIG. 11. In this case, the secondary separator 40 separates the received blood components into leukocytes and the platelet-containing component 100 by performing centrifugal separation and the tertiary separator 42 separates the platelet-containing component 100 into the platelets 104 and the plasma 106 by performing centrifugal separation. Then, the plasma 106 (platelet poor plasma) is stored in the PPP bag 16E first downstream of the tertiary separator 42. Subsequently, the plasma 106 is replaced with the platelet additive solution 102 in the third chamber 52 by the platelet additive solution 102 being supplied to the tertiary separator 42 and the washed platelets 108 with less plasma 106 are stored in the WPC bag 16G along with the platelet additive solution 102. Even with this configuration, the washed platelets 108 with a plasma content of 5% or less can be collected in a satisfactory manner.

Although blood has been used as an example of biological components in the various embodiments described above, the present invention is not limited thereto. Also applicable are, for example, various cells collected or cultured after being collected from a patient or a donor and medical liquids including drugs administered to patients and so on.

FIG. 2
16A PRIMARY SEPARATION BAG
16B ACD SOLUTION STORAGE BAG
16C AUXILIARY BAG
16D ADDITIVE SOLUTION STORAGE BAG
16E PPP BAG
16F DISPOSAL BAG
16G WPC BAG
SECONDARY SEPARATOR
TERTIARY SEPARATOR
RESERVOIR
FIG. 6
S1 ACCOMMODATE WHOLE BLOOD IN FIRST CHAMBER
S2 PERFORM CENTRIFUGAL SEPARATION ON WHOLE BLOOD
S3 TRANSFER BUFFY COAT FROM FIRST CHAMBER TO SECOND CHAMBER
S4 PERFORM CENTRIFUGAL SEPARATION ON BUFFY COAT
S5 TRANSFER PLATELET-CONTAINING COMPONENT FROM SECOND CHAMBER TO THIRD CHAMBER
S6 PERFORM CENTRIFUGAL SEPARATION ON PLATELET-CONTAINING COMPONENT
S7 INTRODUCE PLATELET ADDITIVE SOLUTION INTO THIRD CHAMBER AND REPLACE PLASMA WITH PLATELET ADDITIVE SOLUTION
S8 COLLECT PLATELETS
FIG. 7
PUMP
ON
OFF
CLAMP
CLOSE
OPEN
FIG. 8A
PUMP
ON
OFF
CLAMP
CLOSE
OPEN
FIG. 8B
PLASMA
CENTRIFUGAL FORCE
PLATELET-CONTAINING COMPONENT
FIG. 9A
PUMP
ON
OFF
CLAMP
CLOSE
OPEN
FIG. 9B
PLASMA
PLATELET ADDITIVE SOLUTION
CENTRIFUGAL FORCE
PLATELET ADDITIVE SOLUTION
FIG. 10A
PUMP
ON
OFF
CLAMP
CLOSE
OPEN
FIG. 10B
WASHED PLATELETS
PLATELET ADDITIVE SOLUTION
FIG. 11
16A PRIMARY SEPARATION BAG
16B ACD SOLUTION STORAGE BAG
16C AUXILIARY BAG
16D ADDITIVE SOLUTION STORAGE BAG
16E PPP BAG
16F DISPOSAL BAG
16G WPC BAG
SECONDARY SEPARATOR
TERTIARY SEPARATOR
RESERVOIR
BLOOD COMPONENT
PLATELET-CONTAINING COMPONENT
PLASMA
WASHED PLATELETS

The invention claimed is:
1. A platelet collection method comprising:
conducting whole blood collected from a donor into a first chamber;
separating the whole blood into a first blood component including a large number of platelets and a remaining component by centrifugal separation;
applying at least one centrifugal force during the steps of separating the whole blood and separating the first blood component and
applying a centrifugal force differing from said at least one centrifugal force during the step of separating the platelet-containing component in the third chamber;
transferring the first blood component from the first chamber to a second chamber;
separating the first blood component transferred to the second chamber into a platelet-containing component and a second blood component by centrifugal separation;
transferring the platelet-containing component from the second chamber to a third chamber;
separating the platelet-containing component transferred to the third chamber into platelets and another component by performing centrifugal separation;
introducing a platelet additive solution into the third chamber and replacing the another component with the platelet additive solution; and collecting the platelets remaining in the third chamber along with the platelet additive solution.

2. The platelet collection method according to claim 1, wherein the third chamber has two outlets having different distances from a centrifugal center at the time of the centrifugal separation.

3. The platelet collection method according to claim 1, wherein the blood components flow in sequence from the first chamber through the second chamber to the third chamber through tubes.

4. The platelet collection method according to claim 1, further comprising separating leukocytes in the second chamber as part of the second blood component.

5. The platelet collection method according to claim 1, wherein the platelets remain in the third chamber while the another component flows to an outside of the third chamber and while the platelet-containing component is introduced into the third chamber during the centrifugal separation of the platelet-containing component.

6. The platelet collection method according to claim 5, wherein the another component flows to a reservoir of the remaining component during the centrifugal separation of the platelet-containing component and the another component and the platelet additive solution are allowed to flow to a disposal container during the introduction of the platelet additive solution into the third chamber.

7. The platelet collection method according to claim 1 wherein the platelet-containing component and the platelet additive solution inflow into the third chamber through a single inflow port.

8. The platelet collection method according to claim 7, wherein inflow of the platelet-containing component is stopped during the inflow of the platelet additive solution into the third chamber.

9. The platelet collection method according to claim 1, wherein a speed of inflow of the platelet additive solution into the third chamber is higher during the collection of the platelets than during the replacement of the other component with the platelet additive solution.

10. A platelet collection system comprising:
a primary separation unit including a first chamber for receiving whole blood collected from a donor and for separating the whole blood into a first blood component including a large number of platelets and into a remaining component, said first chamber being adapted to be mounted on a centrifugal separation apparatus;
a secondary separation unit including a second chamber in fluid communication with the first chamber for receiving the first blood component transferred from the primary separation unit and for separating the first blood component into a platelet-containing component and a second blood component, said second chamber being adapted to be mounted on said centrifugal separation apparatus;
a tertiary separation unit including a third chamber in fluid communication with said second chamber for receiving the platelet-containing component transferred from the secondary separation unit and for separating the platelet-containing component into platelets and another component, said third chamber being adapted to be mounted on said centrifugal separation apparatus;
a supply of platelet additive solution in fluid communication with said third chamber;
a first flow path portion allowing the platelet-containing component to flow into the third chamber; and
a second flow path portion allowing the platelet additive solution to flow into the third chamber and
means for introducing the platelet additive solution into the third chamber after an inflow of the platelet-containing component is stopped and for allowing the platelets to flow out of said third chamber along with the platelet additive solution comprising
a first clamp opening and closing the first flow path portion; and
a second clamp opening and closing the second flow path portion, and wherein the second clamp is closed when the first clamp is opened and the second clamp is opened when the first clamp is closed.

11. The platelet collection system according to claim 10 wherein the third chamber comprises a step wall between a first bottom portion and a second bottom portion.

12. The platelet collection system according to claim 11 wherein the third chamber further comprises an inlet port adjacent said first bottom portion, said inlet port being in fluid communication with said supply of platelet additive solution and with said second chamber; and an outlet port adjacent said second bottom portion.

13. A centrifugal blood separation system comprising
a primary separation unit including a first chamber for receiving whole blood collected from a donor and for separating the whole blood into a first blood component including a large number of platelets and into a remaining component, said first chamber being adapted to be mounted on a centrifugal separation apparatus;
a secondary separation unit including a second chamber in fluid communication with the first chamber for receiving the first blood component transferred from the primary separation unit and for separating the first blood component into a platelet-containing component and a second blood component, said second chamber being adapted to be mounted on said centrifugal separation apparatus;
a tertiary separation unit including a third chamber in fluid communication with said second chamber for receiving the platelet-containing component transferred from the secondary separation unit and for separating the platelet-containing component into platelets and another component, said third chamber being adapted to be mounted on said centrifugal separation apparatus; and
a supply of platelet additive solution in fluid communication with said third chamber and
means for introducing the platelet additive solution into the third chamber after an inflow of the platelet-containing component is stopped and for allowing the platelets to flow out of said third chamber along with the platelet additive solution;
a first flow path portion allowing the platelet-containing component to flow into the third chamber; and
a second flow path portion allowing the platelet additive solution to flow into the third chamber; and
said centrifuge separation apparatus comprising
a rotor;
a first clamp opening and closing the first flow path portion; and
a second clamp opening and closing the second flow path portion, and
means for controlling said clamps whereby the second clamp is closed when the first clamp is opened and the second clamp is opened when the first clamp is closed.

* * * * *